Sept. 17, 1946. A. F. ETTER Plant Pat. 710
APPLE TREE
Filed June 23, 1944
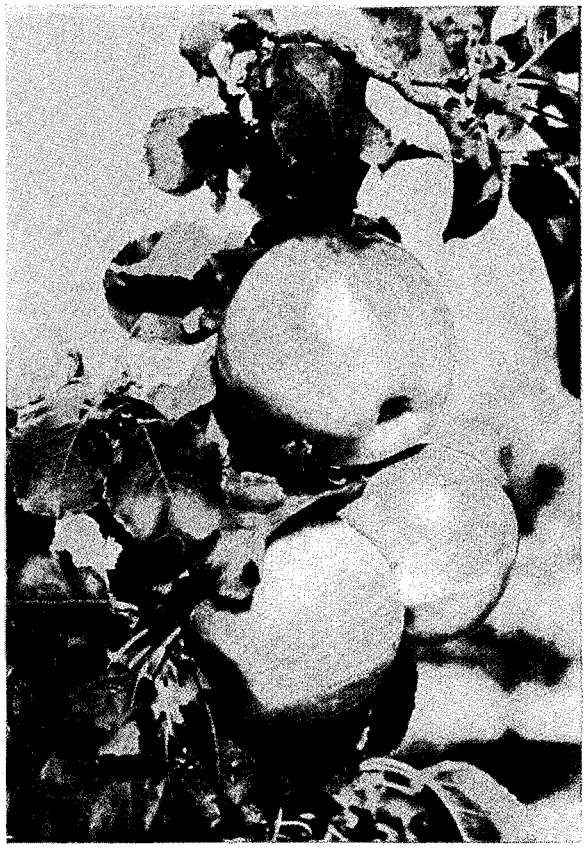
INVENTOR.
ALBERT F. ETTER.
BY
Chas. E. Townsend
ATTORNEY.

Patented Sept. 17, 1946

Plant Pat. 710

UNITED STATES PATENT OFFICE

710

APPLE TREE

Albert F. Etter, Ettersburg, Calif., assignor to George C. Roeding, Jr., Niles, Calif.

Application June 23, 1944, Serial No. 541,690

1 Claim. (Cl. 47—62)

This invention relates to a new variety of apple tree which is a hybrid of the Jonathan and the Baldwin.

In size and shape the fruit of this variety resembles the Baldwin.

The accompanying colored photograph illustrates this new discovery.

The following is a detail description of this new variety:

*Stem of the fruit:* Medium.
*Calyx:* Open.
*Basin:* Medium open.
*Skin:* Medium strong; color, cream, striped red.
*Calyx tube:* Open.
*Core:* Medium large, open.
*Seeds:* Medium large; brown.
*Flesh:* Almost white, unusually tender and juicy.
*Foliage:* Very large, strong, dark green, and healthy.

This apple has a general red tonality and combines the best features of both the Jonathan and the Baldwin. The apple tree develops the large sized fruit of the Baldwin, and the fruit ripens in August and September with the Jonathan. The flesh of the fruit, however, is more crisp than that of either of its parents. This new variety of apple tree is a vigorous grower and of long life.

The foliage of the tree is much darker green than that of the Baldwin. The foliage of the new variety is larger and a deeper green than that of the Jonathan. The tree does not closely resemble any commonly known variety.

What I claim is:

A new variety of apple tree substantially as herein disclosed characterized by the size and shape of its fruit, which is comparable with the Baldwin, with flesh almost white and unusually tender, juicy and crisp.

ALBERT F. ETTER.